United States Patent [19]

Fleury et al.

[11] Patent Number: 5,573,530
[45] Date of Patent: Nov. 12, 1996

[54] HANDLE FOR A SURGICAL INSTRUMENT INCLUDING A MANUALLY ACTUATED BRAKE

[75] Inventors: Michael T. Fleury, Racine; Dean A. Erickson, Greenfield, both of Wis.

[73] Assignee: Cabot Technology Corporation, Wilmington, Del.

[21] Appl. No.: 356,829

[22] Filed: Dec. 15, 1994

[51] Int. Cl.⁶ ........................................ A61B 17/00
[52] U.S. Cl. .................. 606/1; 606/127; 606/113; 606/205
[58] Field of Search ........................ 606/37–50, 1, 606/108, 127, 110, 113, 114, 138–144, 205–211

[56] References Cited

U.S. PATENT DOCUMENTS

| | | | |
|---|---|---|---|
| 1,677,671 | 7/1928 | Councill | 606/127 |
| 3,903,892 | 9/1975 | Komiya | 606/46 |
| 4,815,476 | 3/1989 | Clossick | |
| 5,084,054 | 1/1992 | Bencini et al. | 606/113 |
| 5,282,806 | 2/1994 | Haber et al. | 606/139 |

*Primary Examiner*—Glenn Dawson
*Attorney, Agent, or Firm*—Quarles & Brady

[57] ABSTRACT

A surgical tool, such as grasping forceps, biopsy forceps, or a retaining basket, is operated by a control wire that extends through a sheath. A handle assembly has a luer at one end through which the control wire passes before attaching to a slider that is movably located within an elongated opening in the handle. The slider has a collet mechanism that grips the wire and the luer is rotated to tighten and loosen the collet mechanism. A brake selectively applies a force between the handle and the slider to restrict movement of the slider within the elongated opening of the handle. In different embodiments, the brake is attached to either the handle or the slider and exerts frictional force on the other components. The handle assembly is designed to enable single handed operation of the surgical tool by a user.

33 Claims, 4 Drawing Sheets

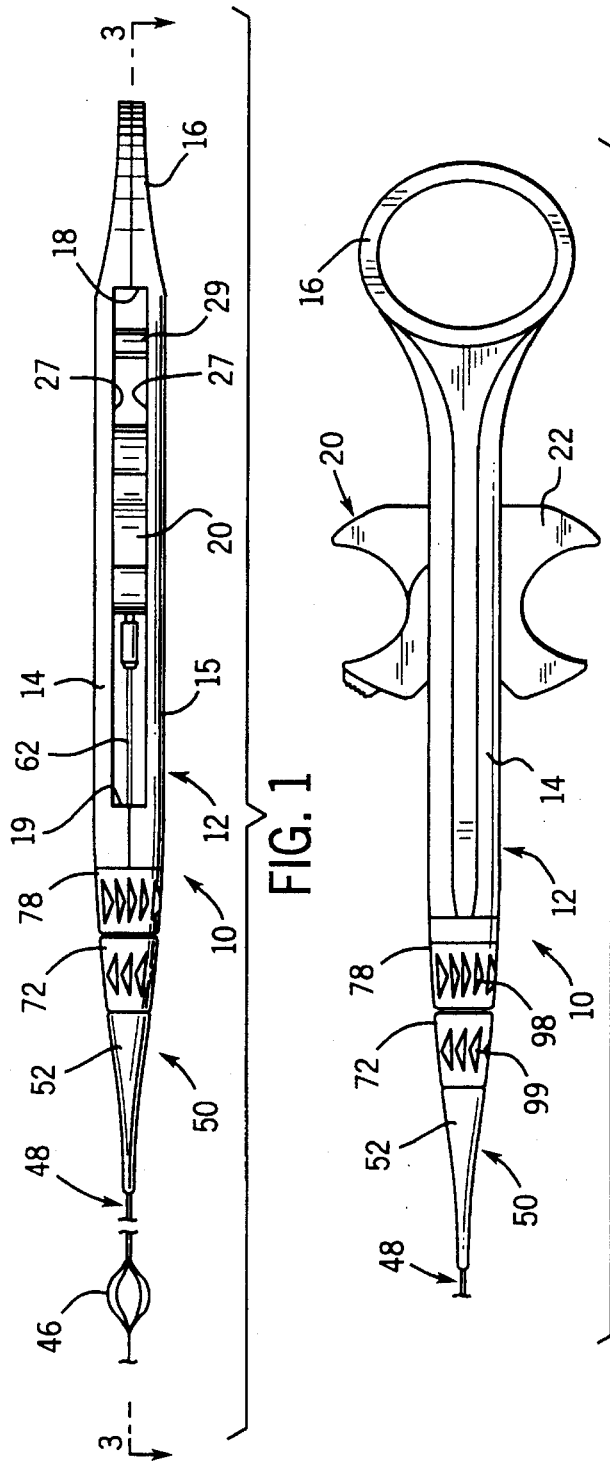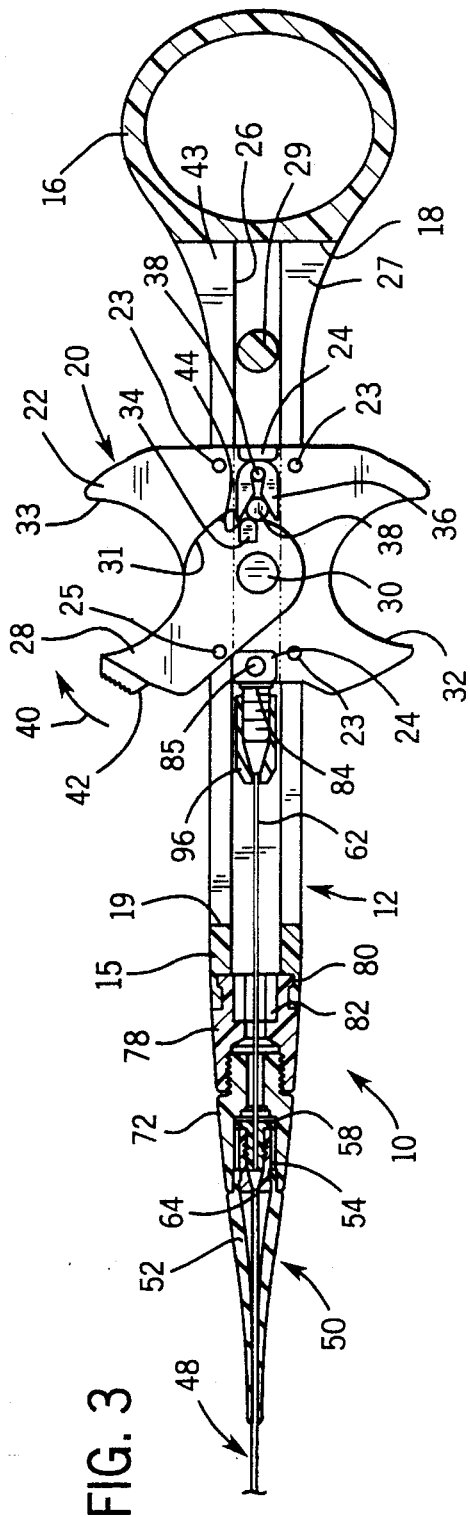

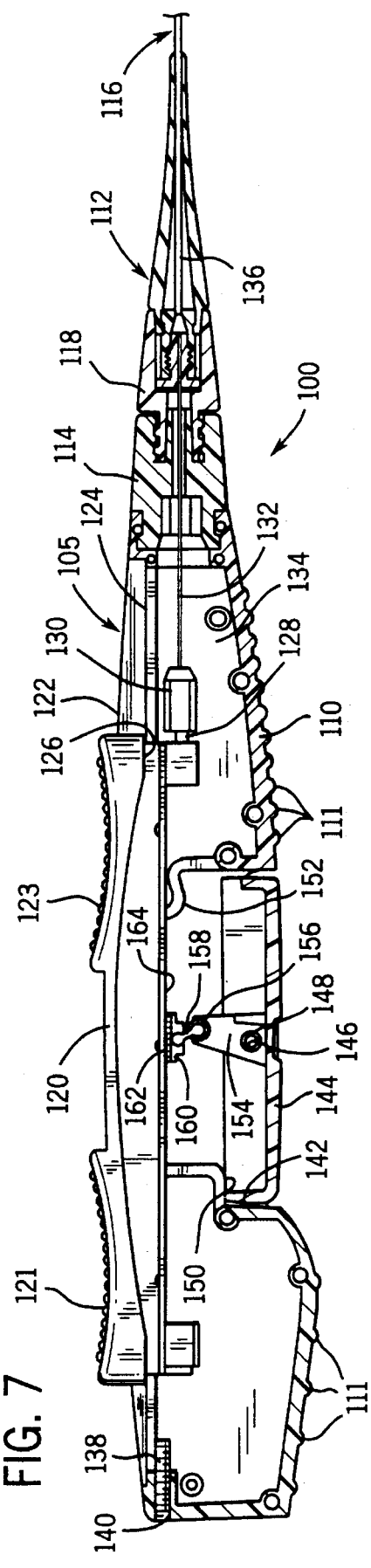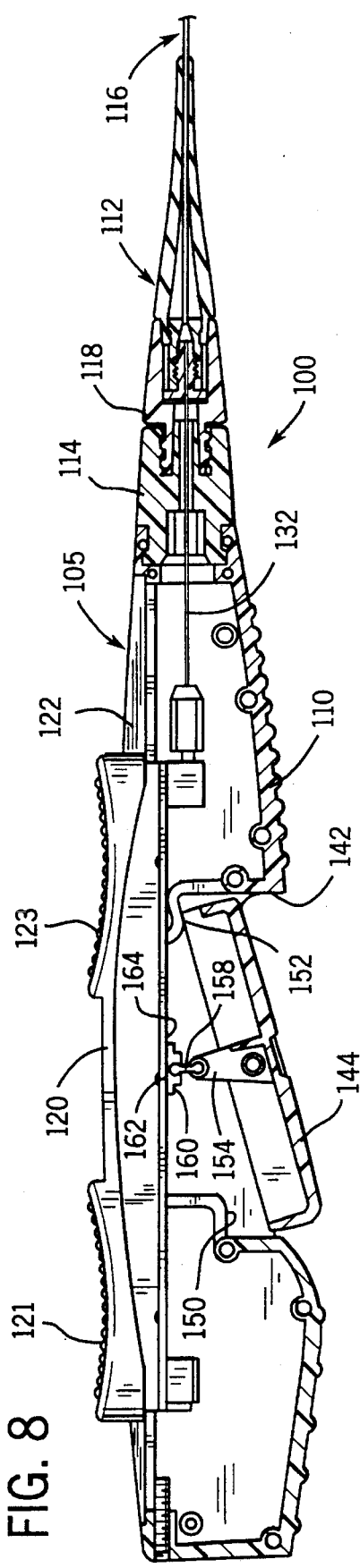

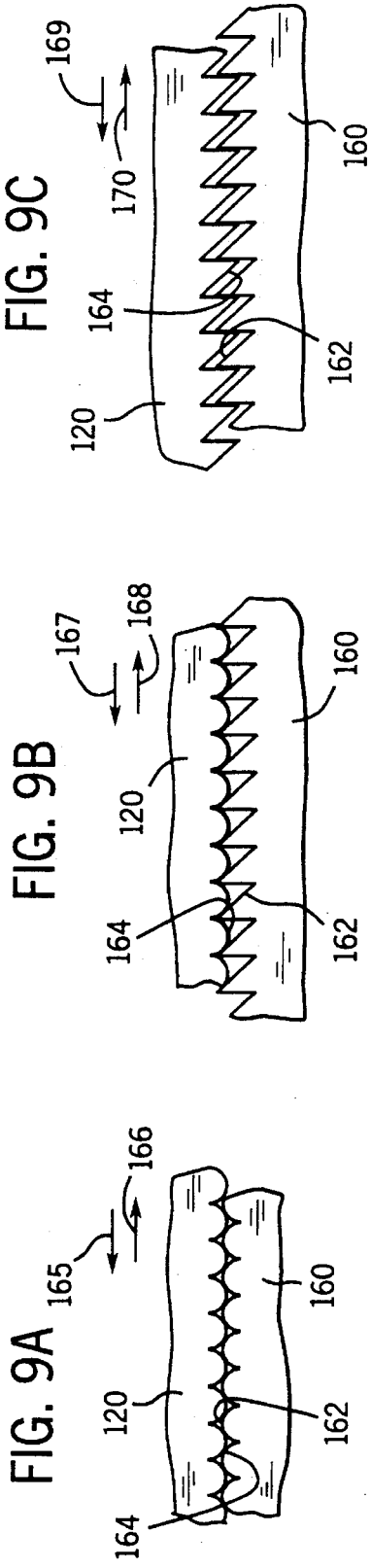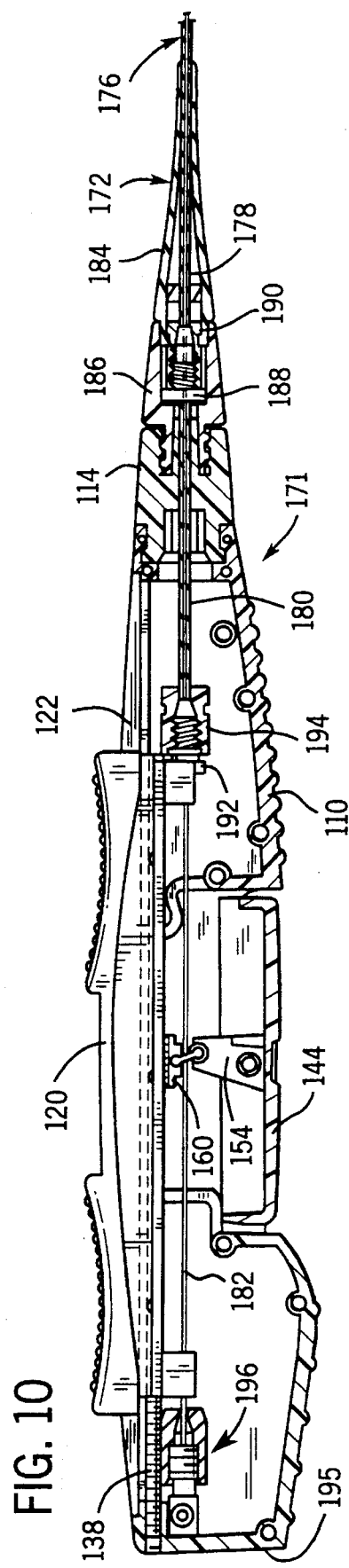

HANDLE FOR A SURGICAL INSTRUMENT INCLUDING A MANUALLY ACTUATED BRAKE

BACKGROUND OF THE INVENTION

The present invention relates to hand-operated surgical instruments, and more particularly to handles for such devices which provide a locking mechanism.

Surgical instruments have been devised wherein a tool, such as a biopsy forceps, grasping forceps or a retaining basket, is attached to the distal end of a guide wire with a handle connected to the guide wire's proximal end. The guide wire is inserted into the patient until the distal end is at the location where a biopsy sample or another object is to be removed. The tool then is operated via a control wire by manipulating the handle and the sample is removed by pulling the guide wire from the patient. For example, instruments of this kind are used to remove kidney stones.

U.S. Pat. No. 4,815,476 discloses a surgical instrument handle assembly having a slider which moves along a handle. The handle includes a ring through which a surgeon places a thumb and the slider has two rings which receive opposing fingers. The proximal end of the guide wire has a sheath that is attached to the handle and a control wire, which passes through the sheath, is connected to the slider. As the surgeon moves the slider with respect to the handle, the control wire moves longitudinally within the sheath. Movement of the slider in one direction causes the control wire to open the tool at the distal end of the guide wire, while opposite movement of the slider closes the tool.

Once the object has been grasped, it is desirable to lock the tool so that the object will not be dislodged during withdrawal from the patient's body. In the aforementioned patent, the control wire passed through a collet at the end of the handle to which the sheath was attached and the control wire then attached to the slider. A nut was tightened onto the collet to grasp the control wire preventing movement with respect to the sheath and thus lock the tool. This type of locking mechanism required the use of two hands to lock and unlock the instrument.

Furthermore, if the tool became caught while being extracted from the patient, further extraction often resulted in tearing of the tissue which was obstructing the tool. Therefore, it is desirable in such situations that the locking mechanism yield allowing the control wire to be pulled through the sheath upon continued attempts to extract the stuck tool.

SUMMARY OF THE INVENTION

The general object of the present invention is to provide a handle assembly for a surgical instrument, such as one having a wire operated effector.

Another object is to provide such a handle assembly that can be operated with a single hand.

A further object is to provide a mechanism that allows the operating wire to be easily attached to and detached from the handle without a need for special tools or disassembly of the handle.

It is desirable, although not essential, to provide the hand-operated surgical instrument with a locking mechanism that yields upon exertion of excessive force.

These and other objects are achieved by a surgical instrument that includes an effector assembly having a sheath with a control member, such as a wire, extending therethrough. An effector element, such as biopsy forceps, grasping forceps or a retaining basket, is formed at the distal end of the control member and operated by movement of the control member within the sheath. A handle has an aperture at one end through which the control member passes. The handle also has an elongated opening within which a slider is movably located and the slider has a mechanism that attaches to the proximal end of the control member.

A brake is provided to selectively apply force between the handle and the slider to restrict movement of the slider within the handle opening. In one embodiment of a surgical instrument according to the present invention, the brake comprises a manually operable lever and a brake shoe both coupled to the slider. The brake shoe is activated by the lever to engage and apply the force against the handle. In another embodiment, the brake comprises a manually operable lever pivotally coupled to the handle and a brake shoe with a surface for engaging the slider to apply the force thereto. A connecting member is pivotally coupled between the lever and the brake shoe to transfer force therebetween. Both embodiments of the surgical instrument enable the surgeon to operate the tool and the locking mechanism with a single hand.

BRIEF DESCRIPTION OF THE DRAWINGS

FIG. 1 is a plane view of one side of a surgical instrument according to the present invention;

FIG. 2 is a plane view of a major side of the surgical instrument;

FIG. 3 is a cross section view along line 3—3 in FIG. 1;

FIG. 7 is a longitudinal cross section through the surgical instrument of FIG. 6 in the unlocked state;

FIG. 8 is a longitudinal cross section through the surgical instrument of FIG. 6 in the locked state;

FIGS. 9A, 9B and 9C illustrate different surfaces of a brake mechanism which interlock to restrict movement of the surgical instrument in the locked state; and FIG. 10 is a longitudinal cross section through a handle according to the second embodiment which has been modified for use with a double sheath effector assembly.

DETAILED DESCRIPTION OF THE INVENTION

Figure 4:
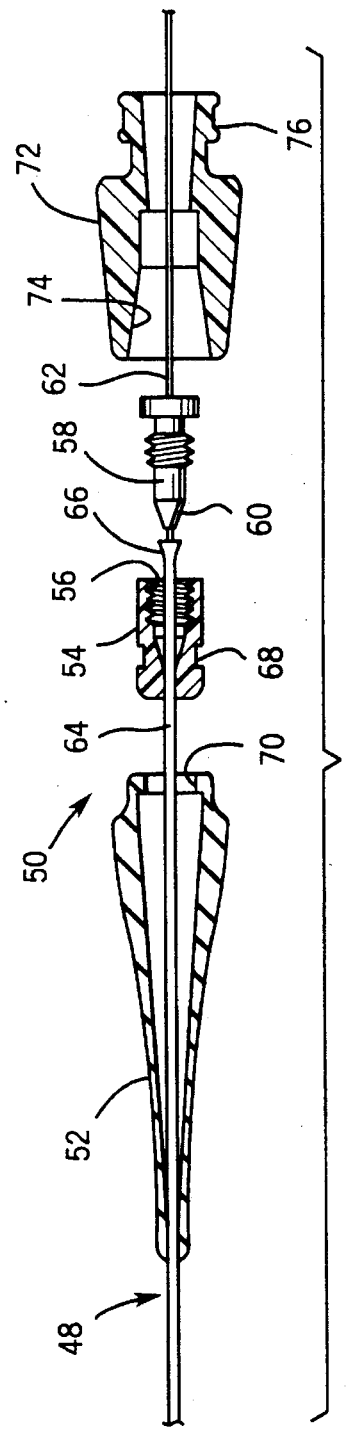
FIG. 4 is an exploded view of components at the handle tip of the surgical instrument.

With initial reference to FIGS. 1 and 2, the handle assembly 10 of a surgical instrument has a handle 12 formed by longitudinal first and second halves 14 and 15 made of plastic. The two halves 14 and 15 are identical except one has pins and the other has holes to receive the pins when the halves are glued together. The assembled handle 12 has an integral thumb receiving ring 16 at one end and couplings at the other end for attaching a guide wire assembly 48 of an effector element such as tool 46.

The assembled handle 12 has an opening 18 between the two halves 14 and 15 with a plastic slider 20 captivated in that opening. As shown in FIG. 3, the slider 20 has a body 22 which has a pair of guide tabs 24 on each of its major surfaces. The guide tabs 24 fit within a longitudinal channel 26 which extends along each half 14 and 15 of the handle 12. The positioning of the tabs 24 in the channels 26 captivates the slider 20 and guides longitudinal movement of the slider along the handle between backstop 29 and end wall 19. The backstop 29 adjusts the length of slider travel to that required for tool operation.

The slider 20 also has a lever arm 28 that fits into a depression in one major surface of the slider body 22 and is pivotally attached thereto by a pin 30. Both of the slider body 22 and lever arm 28 have curved surfaces which combine to form notches 32 and 33 for the opposed fingers of a surgeon. When using the device, the surgeon places a thumb within ring 16 and inserts the index and middle fingers into the notches 32 and 33. In this position, the surgeon is able to operate the instrument with a single hand by moving the slider along the handle 12 with respect to the thumb ring 16.

The slider body 22 with three hemispherical bumps 23 on opposing major surfaces and a fourth hemispherical bump 25 is positioned on the major surfaces of a lever arm 28 that is attached to the body. These bumps 23 and 25 abut longitudinal surfaces 27 of the opening 18 in handle halves 14 and 15 to provide a small amount of resistance to movement of the slider 20 within the opening.

The lever arm 28 of slider 20 has a cam tab 34 which projects slightly from the edge of the lever arm that faces the thumb ring 16. A U-shaped brake shoe 36 is coupled to the slider body 22 so that the open end faces the cam tab 34 and the closed end of the U-shaped brake shoe 36 is held between a pin 38 on the slider body 22 and an adjacent guide tab 24. The brake shoe 36 fits within the channel 26 in the first half 14 of the handle 12. The remote ends of the legs of the brake shoe are tapered and a disc-shaped actuator 38 floats freely between those tapered ends and the cam tab 34 of lever arm 28.

In an unlocked state of the handle assembly 10 shown in FIG. 3, the brake shoe 36 is in a retracted condition and able to slide within the channel 26 of the first half 14 of the handle. In this state, the slider 20 can move freely along the handle 12. To lock the slider 20 with respect to the handle 12, the lever arm 28 is rotated in the direction indicated by arrow 40. This is easily accomplished by the surgeon removing the finger from within the adjacent notch 33 and exerting pressure with the finger on surface 42 to rotate the lever arm in direction 40. As the lever arm rotates, the cam tab 34 pushes the actuator 38 farther into the U-shaped brake shoe 36 causing the legs to spread apart. This action forces the outer surfaces of the brake shoe 36 against the side walls of the channel 26 in the first half 14 of the handle 12. The resultant friction between the brake shoe 36 and the handle 12 restricts movement of the slider 20. Rotation of the lever arm 28 in direction 40 is restricted by abutment of surface 44 with a mating surface of the depression 31 in the major surface of the slider body 22.

To unlock the slider 20 the lever arm 28 is rotated in the direction opposite to the arrow 40. When this occurs, the cam tab 34 no longer presses the actuator 38 into the brake shoe 36 and the resiliency of the brake shoe returns it to the retracted condition in which its outer surfaces no longer engage the channel 26. The cam tab 34 has a tapered tip which cooperates with the resiliency of brake shoe 36 to form an over-the-center spring mechanism that holds the lever arm 28 in the locked and unlocked positions.

The locking and unlocking operations do not transmit linear motion to the guide wire assembly 48 and thus do not affect the position of the tool 46. The handle assembly 10 can be locked even when the guide wire assembly is detached from the handle 12 since the brake is not disassembled when that detachment occurs.

With reference to FIGS. 3 and 4, a coupling mechanism 50 for the wire activated tool 46 is provided at the opposite end of the handle 12 from the thumb ring 16. This mechanism enables a variety of different tools to be attached to the same handle assembly 10. The cable assembly 48 for tool 46 passes through a hollow conical-shaped strain relief 52 at the nose of the handle assembly 10. The strain relief 52 is fabricated of elastomeric material such as silicone rubber and provides smooth, progressive resistance to bending or kinking at the point where the cable assembly 48 exits the handle assembly 10. The cable assembly then enters a tubular sheath lock nut 54 having a central aperture 56 with a tapered portion which opens into a larger diameter threaded portion. The outer surface of the sheath lock nut 54 has an annular recess 68 which receives an inward flange 70 at the larger end of the strain relief 52, thereby attaching the strain relief to the lock nut. A sheath lock screw 58 has a conical tip 60 with axial grooves and a longitudinal aperture through which the control wire 62 of the cable assembly passes. The control wire may be a single strand or a cable formed by twisting several strands together. The control wire 62 extends through a sheath 64, such as a metal coil spring or a polymer tube, that has a flared end 66. In the assembled device when the sheath lock screw 58 is threaded into the aperture 56 in the sheath lock nut 54, the conical tip 60 enters the flared end 66 of the sheath to press that end against the tapered portion of the aperture in the sheath lock nut. This holds the end of the sheath 64 within the coupling mechanism 50 while allowing the control wire 62 to move freely into and out of the sheath. The control wire 62 is but one of several types of control members that can be utilized to operate the tool 46. For example, a solid rod could be placed within the sheath instead of a wire.

After components 52, 54 and 58 have been assembled onto the cable assembly 48, they are inserted and adhesively attached in an aperture 74 of a sheath attachment luer 72, as shown assembled in FIG. 3. The sheath attachment luer 72 has a smaller diameter end projection 76 with external threads.

The projection 76 of the sheath attachment luer 72 threads into an aperture in an end of a tubular wire release luer 78 that is connected to handle 12, thereby connecting the cable assembly 48 to the handle assembly 10. The opposite end of the wire release luer 78 has a smaller diameter portion 80 that extends into an aperture at the end of the handle 12 that is remote from the thumb ring 16. That portion 80 of the wire release luer 78 has an outwardly extending flange that fits within a groove in the aperture in the handle 12 allowing the luer to rotate with respect to the handle.

Figure 5:
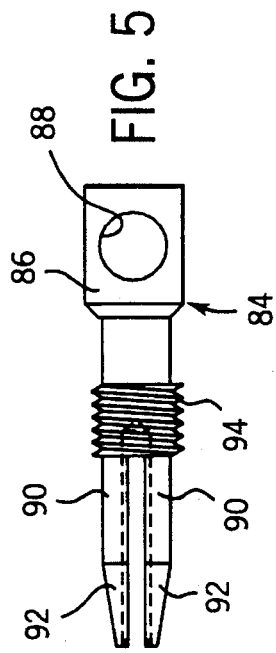
FIG. 5 is a plane view of a collet incorporated in the surgical instrument handle.

Referring to FIGS. 3 and 5, the control wire 62 is attached to the slider 20 by a collet 84 that has a square first end 86 with an aperture 88 therethrough. That first end 86 fits within a square aperture in the slider body 22 and is held in place by a pin 85. The opposite end of the collet 84 has a plurality of longitudinally extending, separated fingers 90 having tapering remote ends 92. The center section 94 of the collet has left-hand, external screw threads onto which a hex nut 96 is threaded. The use of left-hand screw threads inhibits accidental loosening of the collet mechanism. The hex nut 96 has a tapered aperture which engages tapered finger ends 92 and compresses the collet fingers 90 toward one another as the nut is threaded farther onto the collet. When the cable assembly 48 is attached to the handle assembly 10, the proximal end of the control wire 62 extends into the collet 84 between fingers 90 and the collet fingers grip the control wire 62 upon the hex nut 96 being tightened thereon.

The handle assembly 10 can be disconnected from the cable assembly 48 by first detaching the control wire 62 from the collet 84 of the slider 20. This is accomplished by moving the slider 20 toward the tip of the device so that the hex nut 96 enters a hexagonal aperture 82 in the internal end of the wire release luer 78. Although a hexagonal nut and aperture are shown, square, splined, keyed or other non-circular cross section components can be used. Alternatively, the nut and the wire release luer aperture could have non-aligned circular cross sections. By rotating the wire release luer 78 about the handle 12 in the direction indicated by arrows in the outer surface as shown in FIG. 2, the hex nut turns, loosening the collet 84 from the control wire 62. With the control wire released, the sheath attachment luer 72 is turned in the direction indicated by arrows 99 on its outer surface while the wire release luer 78 is held stationary. This action unthreads the sheath attachment luer 72 from the wire release luer 78 and handle 12, enabling the cable assembly 48 and attachment components 52 and 72 to be removed from the handle assembly. As a safety feature, the effector assembly may only be removed from the handle assembly 10 when the tool 46 is in the open position.

The sheath attachment luer 72 is adapted so that it can be removed from the handle 12 and attached to a standard syringe for the injection of a fluid through the sheath 64 to the distal end of the cable assembly 48. The cable assembly then can be removed from the syringe and reattached to the handle by threading the sheath attachment luer 72 into the wire release luer 78. The slider 20 is placed into a position in which the hex nut 98 on collet 84 is within the hexagonal aperture 82 of the wire release luer. The wire release luer 78 is then rotated with respect to the handle 12 in the direction opposite to that indicated by arrows 98 to tighten the nut 96 onto the collet 84 causing the collet to tighten on the end of the control wire 62. Once the surgical instrument has been assembled, moving the slider 20 longitudinally along the handle 12 pulls the control wire 62 farther out of the sheath or pushes it into the sheath to operate the tool, such as wire basket 46, at the distal end of the cable assembly 48.

In the locked state of the handle assembly 10, the brake shoe 36 engages the side walls of channels 26 with sufficient force to hold the slider 20 in place, such as is done after the tool has grasped an object to be extracted. However, the friction between the brake shoe 36 and the handle channel 26 is not so great that the slider 20 cannot move if the tool hits an obstruction within the medical patient. In such case, the tool 46 is allowed to pull on the control wire 62 that is attached to the slider 20 so that the slider will slip along the handle due to the excessive force, rather than holding firm causing the tool to tear tissue at the obstruction.

Figure 6:
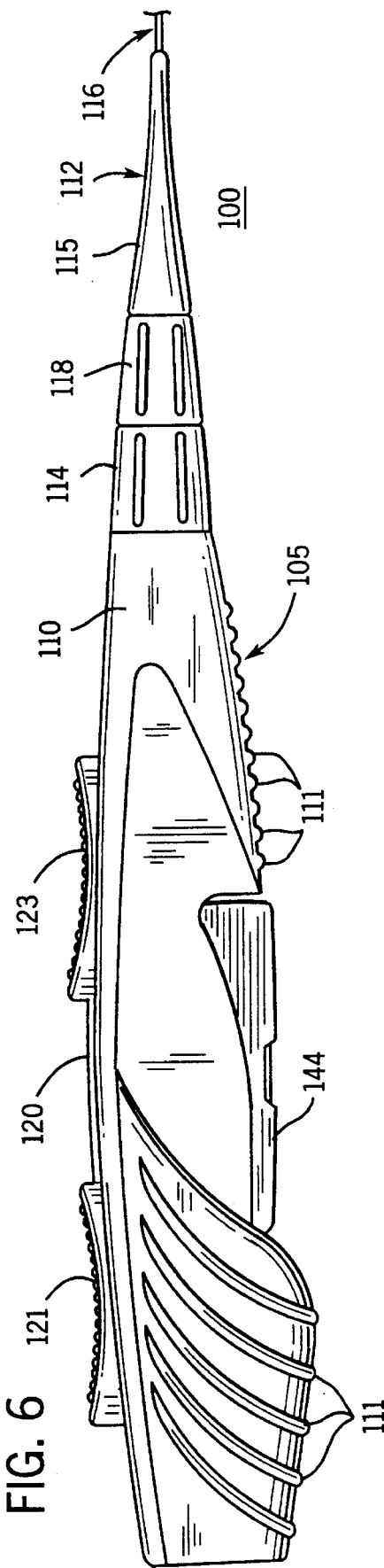
FIG. 6 is a plane view of the side of a second embodiment of a surgical instrument that incorporates the present invention.

FIG. 6 illustrates a second surgical instrument 100 that incorporates the present invention. This surgical instrument 100 comprises a handle assembly 105 with a handle 110 that is formed by two mirror-image, longitudinal halves formed of plastic and cemented together. A nose 112 is formed by a wire release luer 114 attached to the handle 110 in a manner similar to the way in which the wire release luer 78 is rotatably attached to the handle 12 in the previous embodiment. The cable assembly 116 has a strain relief 115 and a sheath attachment luer 118 that screws into the wire release luer 114. Cable assembly 116 and the previously described cable assembly 48 are interchangeable between the two handle assemblies 10 and 105.

With reference to FIGS. 6 and 7, an elongated slider 120 fits within a slot 122 in the top surface of the handle 110 in the orientation of the handle shown in the drawings. A guide rail 124 projects from each of the opposed side walls which form the slot 122 and extends for the full length of the slot. The guide rails 124 fit within grooves 126 that extend along each side of the slider 120 to hold the slider within the slot while guiding movement along the handle.

A collet 128 (identical to the one shown in FIG. 5) is connected to the nose end of the slider 120 and has a hex collet nut 130 attached thereto. When the cable assembly 116 is attached to the handle assembly 105, the control wire 132 extends into a hollow internal cavity 134 within the handle 110 and is grabbed at one end by the collet 128 upon tightening nut 130.

As the slider 120 moves along slot 122, the control wire 132 is pulled out of or pushed into the sheath 136 of the cable assembly 116. A set screw 138 is threaded into an aperture 140 at the opposite end of handle 110 from nose 112. The set screw acts as a stop member for the slider 120 and is adjustable to set the degree of travel for the slider.

The exterior surface of the slider 120 has two concave depressions 121 and 123 with a plurality of ridges on their surface. The underside of the handle 110 also has a plurality of ridges 111. When the user grasps the handle assembly 105, a thumb is placed into one of the concave depressions 121 or 123 of the slider 120 and the remaining fingers of that hand are wrapped around the underside of the handle 110. The ridges on the surface of the slider and the underside of the handle aid the user in grasping the surgical instrument 100 while wearing gloves. By grasping the handle assembly 105 in this manner, the user is able to manipulate the slider 120 using the thumb.

The underside of the handle 110 has a centrally located aperture 142 within which is located a locking lever 144. The locking lever 144 has a center hole 146 which receives pegs extending into the handle cavity 134 from each half of the handle 110. The locking lever 144 pivots about these pegs 148 between a first position illustrated in FIG. 7 where the handle strikes a first stop 150 of the handle, and a second position shown in FIG. 8 in which the lever strikes a second stop 152. As shown in FIG. 7, the locking lever 144 has an arm 154 projecting inward into the handle cavity 134 and offset on one side of the pivot hole 146. The remote end of the arm 154 has a concave retaining depression 156 which forms a circular opening of more than 180°. A connecting member 158 has a dumbbell-like cross section having cylindrical ends with a connecting web there between. One end of the connecting member 158 snaps within the concave retaining depression 156 of the lever arm 154 and is held therein in a manner that permits the connecting member to pivot. The other cylindrical end of the connecting member 158 fits within cylindrical depressions in a pair of brake shoes 160 projecting from the side walls of the handle 110 into the internal cavity 134. Each brake shoe 160 has a surface 162 which is closely spaced from the interior surface 164 of the slider 120. Both surface 162 of the brake shoe 160 and the interior surface 164 of slider 120 have a pattern of fine ribs extending transversely.

In the unlocked state of the handle assembly 105 as illustrated in FIG. 7, a small gap exists between the brake shoe 160 and the slider 120 allowing movement along the slot 122. That movement causes the control cable 132 to be pulled from or pushed into the sheath 136, thereby operating the tool at the remote end of the cable assembly 116.

To lock the surgical instrument 100, the surgeon uses an index finger to pivot the locking lever 144 into the second position illustrated in FIG. 8 in which the locking lever is against the second stop 152 in the handle body. This movement of the locking lever 144 causes the connecting member 158 to be operated by arm 154 thereby exerting an upward force against the brake shoes 160. The brake shoes are flexible with respect to the side walls of the handle from which they project and are pushed upward so that shoe surface 162 abuts the interior surface 164 of the slider 120. This abutment causes the ribs on surfaces 162 and 164 to interlock, restrict movement of the slider 120 along slot 122 of the handle 110. Alternatively, these surfaces can be relatively smooth, yet provide frictional resistance to movement when the surfaces abut.

The ribs on the surfaces 162 and 164 can have different shapes to restrict the movement the slider 120 to various degrees. One pattern of shapes is shown in FIG. 9A where both surfaces 162 and 164 have semi-cylindrical ribs. Because these patterns are symmetrical, the same degree of resistance is provided with respect to movement in opposite directions 165 and 166. Greater restriction to movement can be provided in one direction than in the other by an asymmetrical rib pattern as shown in FIG. 9B. The slider surface 164 has semi-cylindrical ribs while the surface 162 of the brake shoe 160 has a saw tooth rib pattern. The resistance to movement of the slider 120 in direction 168 is greater than in direction 167. In this arrangement the surface pattern prevents the tool 46 from opening while allowing the user to further tighten the tool's grip on an object. By reversing the saw tooth pattern the direction of greater restriction can be changed. FIG. 9C illustrates a saw tooth rib pattern on the surfaces of both the slider 120 and the brake shoe 160 which provide a ratchet action that restricts movement in direction 170 more than in the other direction 169.

The locking lever arm 154 and connecting member 158 cooperate to form an over-the-center spring mechanism which provides a tactile detent feel as the lever is moved between the two positions illustrated in FIGS. 7 and 8. In addition, the over-the-center spring mechanism restricts the locking lever from moving easily between the two positions since the force exerted by the connecting member 158 at an intermediate position of its travel is greater than the force exerted in either the first or second positions illustrated in FIGS. 7 and 8. Thus, the locking lever will not become unlocked unless the surgeon exerts force on the opposite end to pivot the locking lever 144 from the position in FIG. 8 to the position in FIG. 7 in which the handle assembly is unlocked again.

Both embodiments of the surgical instrument are operable by the surgeon with a single hand to move the control wire 62 or 132 as well as lock and unlock the instrument. In addition, their handles 12 and 110 are symmetrical about the longitudinal axis for comfortable operation by right and left-handed people.

FIG. 10 illustrates an embodiment 171 of the second type of surgical instrument for use with a double sheathed effector assembly 172. This surgical instrument 171 comprises the same combination of handle 110, slider 120, locking lever 144 and wire release luer 114 as the instrument 100 in FIGS. 6–8.

The double sheathed effector assembly 172 includes a cable 176 with an outer sheath 178 within which is an inner sheath 180 through which a wire 182 passes. The effector assembly 172 has a strain relief 184 and an outer sheath attachment luer 186 that screws into the wire release luer 114 on handle 110. A hollow outer sheath lock screw 188 is threaded into an outer sheath lock nut 190 so that the screw's conical tip presses a flared end of the outer sheath 178 against a tapered aperture in the sheath lock nut. This securely holds the end of the outer sheath 178 while allowing the inner sheath 180 to move freely through the outer sheath attachment luer 186 in and out of the outer sheath.

The inner sheath 180 in this device acts as a control member and is attached to the slider 120. Specifically an inner sheath lock screw 192, connected to the slider 120, is threaded into an inner sheath lock nut 194 to secure the inner sheath 180 to the slider. The wire 182 of the effector cable 176 passes through the inner sheath lock screw 192 and the inner sheath lock nut 194 and is connected to the opposite end 195 of the handle 110 by a collet and nut assembly 196. The collet and nut assembly 196 is similar to those components used in the previously described surgical instruments.

The wire 182 is attached to the handle 110 and the outer sheath is attached by the outer sheath attachment luer 186 to the handle. When the slider 120 moves relative to handle 110, the inner sheath 180 attached to the slider moves longitudinally along the stationary wire 182 within the stationary outer sheath 178. With this type of double sheath effector assembly 172 the tool at the distal end of cable 176 is operated by movement of the inner sheath 180 with respect to the outer sheath 178 and the wire 182.

We claim:

1. A surgical instrument comprising:

an effector assembly having a sheath with a control member extending therethrough, wherein the control member has proximal and distal ends, and having an effector element formed at the distal end of the control member;

a handle having a first end with an aperture through which the control member passes;

an actuator movably connected to said handle and having a connector that attaches to the proximal end of the control member; and a brake having a lever pivotally coupled to one of said handle and said actuator, and having a brake shoe engaged by the lever to selectively apply a force between said handle and said actuator to restrict movement of said actuator with respect to said handle.

2. The surgical instrument as recited in claim 1 wherein said handle comprises a second end with a receptor for a thumb of a user; and said actuator has a pair of opposing finger receptors formed therein.

3. The surgical instrument as recited in claim 1 wherein said lever is pivotally coupled to said actuator, and said brake shoe is connected to said actuator and activated by said lever to apply the force against said handle.

4. The surgical instrument as recited in claim 1 wherein said handle further includes an elongated opening; and said actuator is a slider movably located within the elongated opening of said handle.

5. The surgical instrument as recited in claim 4 wherein:

said handle includes a wall with a channel therein;

the lever of said brake is pivotally coupled to said slider and has a cam surface;

the brake shoe has a U-shape with two legs and coupled to said slider so as to be located within the channel of said handle; and further comprising an activator positioned between the legs of the brake shoe and adjacent to the cam surface of the lever, wherein pivotal movement of the lever causes the cam surface to push the activator into the brake shoe which spreads the legs apart and against surfaces which form the channel in said handle.

6. The surgical instrument as recited in claim 1 wherein said lever is pivotally coupled to said actuator and has a cam surface that exerts the force in response to movement of said lever.

7. The surgical instrument as recited in claim 1 wherein the connector of said actuator comprises a collet within which is received the proximal end of the control member; and a nut which engages said collet to grab the control member.

8. The surgical instrument as recited in claim 7 further comprising a wire release luer rotationally attached to the first end of said handle and having an aperture with a non-circular cross section for receiving said nut, wherein rotation of said wire release luer while said nut is received therein tightens or loosens said nut on said collet depending upon a direction of rotation.

9. The surgical instrument as recited in claim 8 wherein said effector assembly further comprises a sheath attachment luer attached to a proximal end of the sheath and releasably connected to said wire release luer.

10. The surgical instrument as recited in claim 1 wherein said effector assembly further comprises a sheath attachment luer attached to a proximal end of the sheath and releasably connected to said handle.

11. The surgical instrument as recited in claim 1 further comprising a stop member adjustably coupled to said handle for limiting movement of said actuator.

12. The surgical instrument as recited in claim 1 wherein:
said handle has an elongated opening with a guide rail extending along a wall which forms the elongated opening; and
said actuator is a slider having a groove within which the guide rail is received.

13. The surgical instrument as recited in claim 1 wherein said brake prevents movement of said actuator with respect to said handle until force exerted on said actuator exceeds a threshold level above which movement occurs.

14. The surgical instrument as recited in claim 1 wherein said actuator is able to move in first and second directions with respect to said handle; and said brake provides greater resistance to movement in the first direction than to movement in the second direction.

15. The surgical instrument as recited in claim 1 wherein:
said lever is pivotally coupled to said handle;
said brake shoe has a surface for releasably engaging a surface of said actuator; and
further comprising a connecting member coupled between said lever and said brake shoe to transfer force from said lever to said brake shoe.

16. The surgical instrument as recited in claim 15 wherein said lever is attached to and projects from said handle.

17. The surgical instrument as recited in claim 1 wherein said actuator has a surface with ribs; and said brake has a surface with ribs, which mesh with the ribs of said actuator to restrict movement of said actuator with respect to said handle.

18. The surgical instrument as recited in claim 17 wherein the ribs on at least one of said actuator and said brake are asymmetrical.

19. The surgical instrument as recited in claim 17 wherein the ribs on at least one of said actuator and said brake are saw tooth shaped.

20. A surgical instrument comprising:
an effector assembly having a sheath with a control member extending therethrough, wherein the control member has proximal and distal ends, and an effector element formed at the distal end of the control member;
a handle having a first end with an aperture through which the control member passes, said handle having an elongated opening with a wall of which having a channel therein;
a slider movably located in the elongated opening of said handle, and having a collet within which is received the proximal end of the control member and a nut which engages said collet thereby causing said collet to grab the control member; and
a brake that applies force between said slider and surfaces of the channel to restrict movement of said slider within the elongated opening of said handle.

21. The surgical instrument as recited in claim 20 wherein said brake comprises:
a lever pivotally coupled to said slider and having a cam surface;
a brake shoe having a U-shape with two legs and attached to said slider so as to be located within the channel of said handle; and
an actuator positioned between the legs of said brake shoe and adjacent to the cam surface of said lever, wherein pivotal movement of said lever causes the cam surface to push said actuator into said brake shoe which spreads the legs apart and against surfaces of the channel in said handle.

22. The surgical instrument as recited in claim 20 further comprising a wire release luer rotationally attached to the first end of said handle and having an aperture with a non-circular cross section for receiving said nut, wherein rotation of said wire release luer while said nut is received therein tightens or loosens said nut on said collet depending upon a direction of rotation.

23. A surgical instrument comprising:
an effector assembly having a sheath with a control member extending therethrough, wherein the control member has proximal and distal ends, and an effector element formed at the distal end of the control member;
a handle having a first end with an aperture therethrough within which the proximal end of the control member is received, said handle having an elongated opening with a guide rail extending along a wall which forms the elongated opening;
a slider movably located within the elongated opening of said handle, and having a groove within which the guide rail is received, said slider including a connector that attaches to the proximal end of the control member; and
a brake that applies force between said handle and said slider to restrict movement of said slider within the elongated opening of said handle, said brake includes: a lever pivotally coupled to said handle, a brake shoe having a surface for engaging a surface of said slider to apply the force thereto, and a connecting member coupled between said lever and said brake shoe to transfer force from said lever to said brake shoe.

24. The surgical instrument as recited in claim 23 wherein said lever has an arm with a notch at one end within which said connecting member is received.

25. A surgical instrument comprising:
an effector assembly having an outer sheath, an inner sheath extending through the outer sheath and a wire extending through the inner sheath, and having an effector element;

a handle assembly having a handle, a first connector which attaches the outer sheath to the handle, and a second connector which attaches the wire to the handle;

an actuator movably connected to said handle and having a third connector that attaches to the inner sheath; and a brake that selectively applies a force between said handle and said actuator to restrict movement of said actuator with respect to said handle.

26. The surgical instrument as recited in claim 25 wherein said brake comprises:

a lever pivotally coupled to said handle;

a brake shoe having a surface for releasably engaging a surface of said actuator and a connecting member coupled between said lever and said brake shoe to transfer force from said lever to said brake shoe.

27. A surgical instrument handle assembly, for operating a tool connected to a control member, said surgical instrument handle assembly comprising:

a handle having a first end with an aperture for receiving therethrough the control member and having an elongated opening;

a slider movably located within the elongated opening of said handle and having a connector for attaching to the control member; and a brake having a lever pivotally coupled to one of said handle and said slider, and having a brake shoe engaged by the lever to selectively apply a force between said handle and said slider to restrict movement of said slider within the opening of said handle.

28. The surgical instrument handle assembly as recited in claim 27 wherein said lever is pivotally coupled to said slider, and said brake shoe is connected to said slider and activated by said lever to apply the force against the handle.

29. The surgical instrument handle assembly as recited in claim 27 wherein:

said handle includes a channel in a wall which forms the elongated opening;

said lever is pivotally coupled to said slider and has a cam surface;

said brake shoe has a U-shape with two legs and coupled to said slider so as to be located within the channel of said handle; and further comprising an activator positioned between the legs of said brake shoe and adjacent to the cam surface of said lever, wherein pivotal movement of said lever causes the cam surface to push said activator into said brake shoe which spreads the legs apart and against surfaces which form the channel in said handle.

30. The surgical instrument handle assembly as recited in claim 27:

wherein the connector of said slider comprises a collet adapted to receive the proximal end of the control member; and a nut which engages said collet for grabbing the control member; and further comprising a wire release luer rotationally attached to the first end of said handle and having an aperture with a non-circular cross section for receiving said nut, wherein rotation of said wire release luer while said nut is received therein tightens or loosens said nut on said collet depending upon a direction of rotation.

31. The surgical instrument handle assembly as recited in claim 27 wherein:

said handle has a guide rail extending along a wall which forms the elongated opening; and said slider has a groove within which the guide rail is received.

32. The surgical instrument handle assembly as recited in claim 27 wherein:

said lever is pivotally coupled to said handle;

said brake shoe has a surface for releasably engaging a surface of said slider; and further comprising a connecting member coupled between said lever and said brake shoe to transfer force from said lever to said brake shoe.

33. The surgical instrument handle assembly as recited in claim 27 wherein said connector of said slider is adapted to provide removable attachment to the control member without requiring disassembly of said handle assembly.

* * * * *